United States Patent
Goria

(10) Patent No.: US 8,500,625 B2
(45) Date of Patent: *Aug. 6, 2013

(54) SURGICAL KIT FOR TREATING URINARY INCONTINENCE IN MAN

(75) Inventor: Vincent Goria, Lyons (FR)

(73) Assignee: CL Medical, Sainte Foy Les Lyon (FR)

( * ) Notice: Subject to any disclaimer, the term of this patent is extended or adjusted under 35 U.S.C. 154(b) by 704 days.

This patent is subject to a terminal disclaimer.

(21) Appl. No.: 11/882,674

(22) Filed: Aug. 3, 2007

(65) Prior Publication Data

US 2008/0076963 A1    Mar. 27, 2008

Related U.S. Application Data

(60) Provisional application No. 60/878,080, filed on Jan. 3, 2007.

(30) Foreign Application Priority Data

Sep. 21, 2006   (FR) ...................... 06 08275

(51) Int. Cl.
    *A61F 2/00*   (2006.01)
(52) U.S. Cl.
    USPC ............................ 600/37; 600/30
(58) Field of Classification Search
    USPC .................. 600/37, 29–31; 606/151–158
    IPC ....................................... A61B 17/08
    See application file for complete search history.

(56) References Cited

U.S. PATENT DOCUMENTS

| | | | | |
|---|---|---|---|---|
| 6,039,686 A | * | 3/2000 | Kovac | 600/30 |
| 6,042,536 A | * | 3/2000 | Tihon et al. | 600/37 |
| 6,382,214 B1 | * | 5/2002 | Raz et al. | 128/898 |
| 6,383,201 B1 | | 5/2002 | Dong | |
| 6,408,656 B1 | | 6/2002 | Ory et al. | |
| 6,599,318 B1 | * | 7/2003 | Gabbay | 623/11.11 |
| 6,612,977 B2 | | 9/2003 | Staskin et al. | |
| 6,652,450 B2 | * | 11/2003 | Neisz et al. | 600/30 |
| 6,695,855 B1 | | 2/2004 | Gaston | |
| 7,175,591 B2 | * | 2/2007 | Kaladelfos | 600/37 |
| 7,407,480 B2 | * | 8/2008 | Staskin et al. | 600/30 |
| 7,762,942 B2 | * | 7/2010 | Neisz et al. | 600/30 |
| 2002/0138025 A1 | | 9/2002 | Gellman et al. | |

(Continued)

FOREIGN PATENT DOCUMENTS

| | | |
|---|---|---|
| EP | 1 342 450 A1 | 9/2003 |
| EP | 1342450 | 1/2007 |

(Continued)

*Primary Examiner* — Charles A Marmor, II
*Assistant Examiner* — Catherine E Burk
(74) *Attorney, Agent, or Firm* — Dowell & Dowell, PC

(57) ABSTRACT

The surgical kit comprises at least one elongate strip for supporting the urethra of a patient, the strip comprising a knit of yarns forming empty spaces between one another, at least in the longitudinal middle portion of the strip that is to extend transversely under the urethra when the strip is implanted, said knit comprising both reinforcement constituted by longitudinal chains and an intermediate trellis transversely interconnecting the chains. In order to guarantee light obstructive support of the urethra, the treatment kit further comprises suture means adapted to be connected to the chains of the knit by being passed through the empty spaces so as to join the middle portion of the strip with the anatomical tissue under the urethra at at least two connection spots in alignment in a direction that is substantially perpendicular to the longitudinal direction of the strip.

13 Claims, 5 Drawing Sheets

U.S. PATENT DOCUMENTS

| | | |
|---|---|---|
| 2003/0045774 A1 | 3/2003 | Staskin et al. |
| 2004/0144394 A1 | 7/2004 | Dauner et al. |
| 2004/0215219 A1 | 10/2004 | Eldridge et al. |
| 2005/0070829 A1 | 3/2005 | Therin et al. |
| 2005/0222591 A1* | 10/2005 | Gingras et al. ............... 606/151 |
| 2005/0250977 A1 | 11/2005 | Montpetit et al. |
| 2006/0195010 A1* | 8/2006 | Arnal et al. ................... 600/30 |
| 2006/0252980 A1* | 11/2006 | Arnal et al. ................... 600/29 |
| 2006/0287571 A1* | 12/2006 | Gozzi et al. ................... 600/30 |
| 2008/0210247 A1* | 9/2008 | De Leval ...................... 128/885 |

FOREIGN PATENT DOCUMENTS

| | | |
|---|---|---|
| EP | 1797842 | 6/2007 |
| FR | 2792824 | 11/2000 |
| WO | 2007/016698 | 2/2007 |
| WO | 2007/149593 | 12/2007 |

* cited by examiner

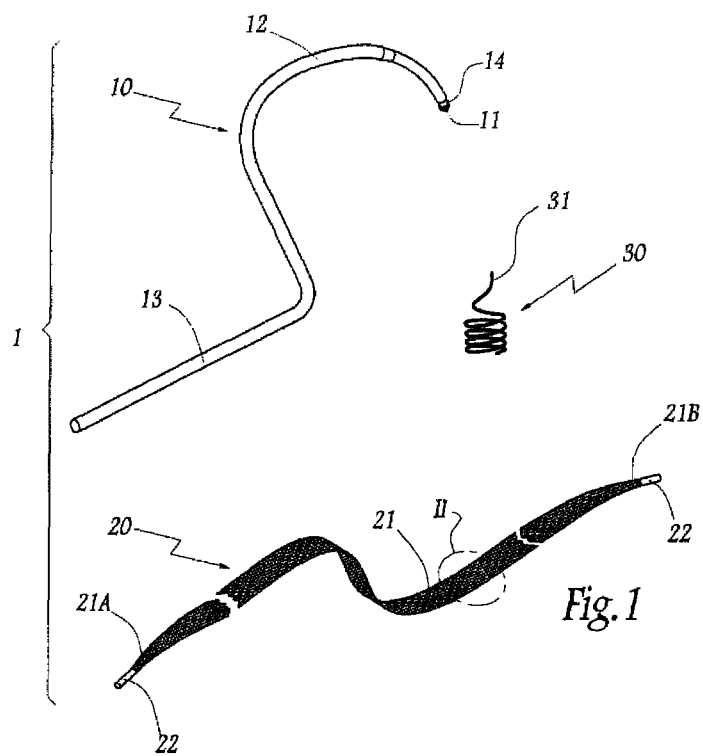
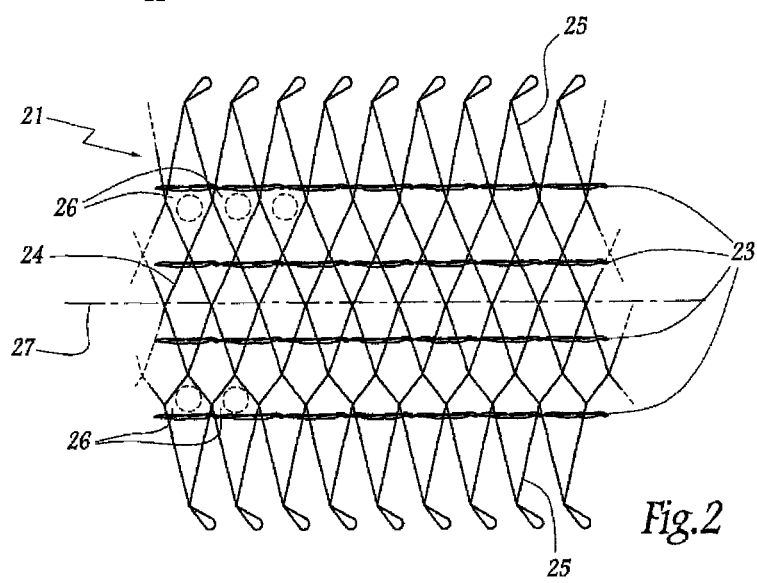

SURGICAL KIT FOR TREATING URINARY INCONTINENCE IN MAN

CROSS REFERENCE TO RELATED APPLICATIONS

This application claims the benefit on U.S. Provisional Patent Application 60/878,080, filed Jan. 3, 2007 in the name of the same inventor, the contents of which are incorporated herein by reference, and also claims priority on French Application 06 08275 filed Sep. 21, 2006.

BACKGROUND OF THE INVENTION

1. Field Of The Invention

The present invention relates to a surgical kit for treating urinary incontinence in a man, to the use of such a kit, and to a surgical method of treating urinary incontinence in a man by means of the kit. The invention also relates to a strip for supporting the urethra of a man in order to treat incontinence.

Urinary incontinence in man after prostatectomy is a debilitating condition that reduces quality of life, even when incontinence is moderate. The number of incontinent patients has increased in the last few years with the advent of facilities for early detection of cancer of the prostate and with a greater number of total prostatectomies being performed. Even though recent operative techniques make it possible to preserve the sphincter better, leaks of urine can occur in a non-negligible percentage of cases: these leaks of urine are associated with the surgical technique which sections the low portion of the prostate in the immediate vicinity of the sphincter, but they can also be encouraged by elements particular to the patient, such as a short urethra, a weak or easily-tired sphincter, etc.

For patients suffering from urinary incontinence in spite of retraining of their sphincter, the surgical treatment that has commonly been employed in the last few years consists in implanting an artificial sphincter. This surgery significantly limits incontinence, but it suffers from major drawbacks: the patient must manipulate a pump on each miction, the implanted equipment is onerous, and the repeat surgery rate is high.

A novel surgical treatment technique has thus appeared in the last few years, namely installing a supporting implant under the urethra, the implant generally being in the form of a plate-shaped net. That kind of net needs to be firmly secured to the anatomical structures of the patient in order to guarantee effective support of the urethra and thus correct incontinence.

2. Brief Description Of The Related Art The plate is thus either suspended by threads rising on either side of the bladder over or behind the pubic bone, with terminal fastenings in the patient's abdominal wall, or else they are secured directly by screws placed in the bony ischio-pubic branches of the patient. The first configuration leads to real risks of perforating the bladder, and the second configuration, comprising surgery that is more complex, exposes the patient to risks of ostitis. In both configurations, the presence of an implanted plate can lead to postoperative perineal discomfort that is transient or to perineal pain that is permanent. Furthermore, even if the success rate of the treatment is high in the short term, it tends to drop significantly over time.

Simultaneously, the equipment and methods used for surgical treatment of incontinence in women have been successively developed over the last few years. In particular, EP-A-1 342 450 in the name of the present Applicant discloses a strip for sub-urethral support that can be implanted, amongst other approaches, by a so-called "transobturator" approach, i.e. by passing the free end portions of the strip through the respective obturator foramens of the pelvic bone of a patient, thus having the effect of suspending the urethra by means of the longitudinal middle portion of the strip. The advantages of this transobturator approach for implantation are real, since they run no risk of perforating the bladder and they do not require any fastening to bone, with only the free ends of the strip being secured to the abdomen of the patient.

SUMMARY OF THE INVENTION

Likewise in the field of treating incontinence in women, FR-A-2 859 624 and US-A-2002/0138025 propose knitted strips in which the middle portion forms flexible support for the urethra, while the longitudinal ends of the strip are firmly anchored in the body of the patient at a distance from the urethra, in particular by means of sutures. The strips proposed in those two documents give results that are satisfactory in woman, but that unusable or even dangerous in man. The strip of FR-A-2 859 624 is knitted so that its middle portion is significantly more elastic than its ends in which the density of the knitting is considerably increased in order to make said ends strong and allow them to be anchored. Such a disposition is advantageous for woman, but turns out to be counterproductive for man whose urethra must be firmly supported in order to reestablish continence. Similarly, the strip of US-A-2002/0138025 is knitted in the form of a uniform trellis that thus presents mechanical properties of elasticity that are isotropic, i.e. substantially identical in all directions. Such a disposition is not desirable for man since the stresses of longitudinal traction that would need to be applied to the strip for supporting the urethra sufficiently firmly would lead to the knit lengthening and thus becoming narrower, with a real risk of damaging the urethra by a "cheese-wire" effect.

The object of the present invention is to provide a surgical kit for treating urinary incontinence in a man that is effective, easy to manipulate, in particular concerning securing it in the patient's body, and that can be put into place using a transobturator approach.

To this end, the invention provides a surgical kit for treating urinary incontinence in a man, the kit comprising:
  at least one elongate strip for supporting the urethra of a patient, the strip comprising a knit of yarns that form empty spaces between one another, at least in the longitudinal mid-portion of the strip for extending transversely under the urethra when the strip is implanted, said knit comprising both reinforcement constituted by longitudinal chains and an intermediate trellis interconnecting the chains transversely; and
  suture means suitable for being connected to the chains of the knit and being fitted through the empty spaces so as to join the middle portion of the strip to anatomical tissue under the urethra at least two connection spots that are in alignment in a direction that is substantially perpendicular to the longitudinal direction of the strip.

The use of a strip that is elongate enables the strip to be implanted close to the anatomical tissue under the urethra, in particular close to the spongy body surrounding the urethra and to the cavernous bodies disposed on either side of the spongy body. Because of its small width, in particular compared with plate-type implants, it is possible to separate the anatomical structures of the patient more deeply without complicating the surgical acts. The shape of the elongate strip also enables the strip to be implanted by a transobturator approach, with each free end portion of the strip being capable of being passed through one of the obturator foramens of the patient's pelvic bone, thus causing the strip to present an overall U-shape producing an effective support effect for the urethra which is situated at the bottom of the U-shape. Although the transobturator implantation approach used by the surgical kit of the invention might, at first glance, appear to be equivalent to the transobturator approach used in treating urinary incontinence in woman, it should be recalled that the constraints associated with securing such a strip in man are quite opposite to those in woman: in woman, the strip is implanted so as to remain flexible in the vicinity of the pelvic floor, since the anatomy of the lower abdomen in woman does not require and cannot accept any firm anchoring such as anchoring by suturing. On the contrary, in man, the spongy body surrounding the urethra presents a degree of firmness, and effective support for the urethra in order to treat incontinence requires clear pressure under tension from the strip against the spongy body, or more generally against the anatomical tissue under the urethra, thereby dissuading the person skilled in the art, a priori, from transposing to man the technique developed for woman. One of the essential ideas on which the invention is based is to take advantage of the knitted structure of the strip, at least in its longitudinal middle portion, for enabling said middle portion to be sutured directly to the anatomical tissue under the urethra, and in particular to the spongy body. The suturing means used, such as suture threads, pass easily through the empty spaces formed between the yarns of the knit, without damaging the knitted structure, e.g. by tearing it. The invention makes provision for connecting the sutures to the longitudinal chains forming the reinforcement of the knit, organizing the connection spots in one or more groups of at least two spots each, the spots in each group being aligned perpendicularly to the longitudinal direction of the strip: while the strip in being implanted, applying traction to each end of the strip creates, in the bottom of the U-shape formed by the longitudinal middle portion of the strip around the tissue under the urethra, an effect of giving the urethra transverse support that is uniform and well controlled, and that by virtue of the sutured connection spots tends to obstruct the urethra partially so as to treat incontinence. The presence of the longitudinal chains enables the knit to be sutured reliably, while also withstanding traction without deforming in width. It can be understood that the knitted structure with longitudinal chains of the middle portion of the strip makes it possible both to suture it accurately and reliably to the tissue under the urethra and to apply a high level of traction thereto, including in the sutured zones, as is needed for reestablishing continence.

By suturing the middle portion of the strip, it is also possible to avoid any subsequent migration thereof, in particular in a rearward direction. In addition, the empty spaces formed between the yarns of the knit facilitate tissue colonization, which explains why the suture means used may be resorbable.

According to other advantageous characteristics of the surgical kit of the invention, taken in isolation or in any technically feasible combination:

each empty space of the knit, through which the suture means are to pass, has dimensions enabling a circle having a diameter of at least 1 millimeter (mm) to be geometrically inscribed therein;

the knit and the suture means are adapted to be connected to each other at four connection spots for connection to the chains of the knit so as to form a pattern of rectangular or square shape, having a midline that is substantially perpendicular to the longitudinal direction of the strip and that is situated in the sagittal midplane of the urethra;

the knit and the suture means are adapted to position both or at least two of the connection spots for connection to the chains of the knit in the sagittal midplane of the urethra;

the knit and the suture means are adapted to position each connection spot for connection to the chains of the knit closer to one of the side edges of the strip than to its center line;

the strip is constituted over its entire length by the knit;

the yarns of the knit are polypropylene monofilaments;

the suture means comprise suture threads that are individually connected to the knit via respective corresponding connection spots;

the suture means are resorbable;

at least two strips are provided suitable for being implanted adjacent each other lengthwise, being connected to each other via their respective adjacent edges, possibly at least one of the connection spots then engaging one of the chains of the knit of each of the strips.

The invention also provides a use of a surgical kit as defined above, to obtain an implanted kit for treating incontinence in a man.

The invention also provides an elongate strip for supporting the urethra of a man for treating urinary incontinence, the strip comprising a knit of yarns that form between them empty spaces, at least in the longitudinal mid-portion of the strip extending transversely under the urethra, the knit comprising both reinforcement constituted by longitudinal chains and an intermediate trellis transversely interconnecting the chains, said chains having suture means connected thereto by passing through the empty spaces so as to join the middle portion of the strip with anatomical tissue under the urethra at least two connection spots in alignment in a direction that is substantially perpendicular to the longitudinal direction of the strip.

The definition of this strip corresponds to the strip of the surgical kit as defined above, when implanted in a man.

The invention also provides a surgical method of treating urinary incontinence in a man, by means of a strip for supporting the urethra of a patient, said strip comprising a knit of yarns that form empty spaces between one another, at least in a longitudinal mid-portion of the strip, said knit comprising both reinforcement constituted by longitudinal chains and an intermediate trellis interconnecting the chains transversely, and said method comprising the following operative steps:

i) vertically incising the skin and the subcutaneous fat in the perineal region of the patient, between the scrotum and the anus, up to the bulb of the urethral spongy body, while preserving the spongy body;

ii) in the perineal incision made during step i), separating the two cavernous bodies of the patient on either lateral side of the urethral spongy body;

iii) sagittally incising the perineal membrane between each of the two cavernous bodies and the urethral spongy body;

iv) putting the strip into place in the patient's body so that the middle portion of the strip extends under and across the urethral spongy body while, on either side of said middle portion, each remaining portion of the strip extends from the corresponding incision in the perineal membrane made in step iii) to the root of the patient's corresponding thigh, passing through the corresponding obturator foramen of the patient's pelvic bone, the free ends of the strip projecting out from the patient from the respective roots of each of the thighs;

v) pulling on the two free ends of the strip so as to cause the knit of the middle portion of the strip to bear under tension against the urethral spongy body;

vi) fitting suture means through the empty spaces of the knit and connecting the suture means to the chains of the knit so as to join the middle portion of the strip with the anatomical tissue under the urethra, in particular the urethral spongy body, at least two connection spots in alignment in a direction that is substantially perpendicular to the longitudinal direction of the strip; and vii) sectioning the ends of the strip that project out at the roots of the thighs and closing the perineal incision made in step i).

According to advantageous characteristics of this method:
during step vi), the connection spots to the chains are made so as to form a pattern of rectangular or square shape, with a midline that is substantially perpendicular to the longitudinal direction of the strip that is situated in the sagittal midplane of the urethra;
step v) is performed before step vi); and
step v) is performed at least in part after performing all or part of step vi).

BRIEF DESCRIPTION OF DRAWINGS

The invention can be better understood on reading the following description given purely by way of example and made with reference to the drawings, in which:

FIG. 1 is a diagrammatic perspective view of a surgical kit of the invention;

FIG. 2 is a diagrammatic elevation vie showing the detail in circle II of FIG. 1;

DESCRIPTION OF THE PREFERRED EMBODIMENT

Figure 3:
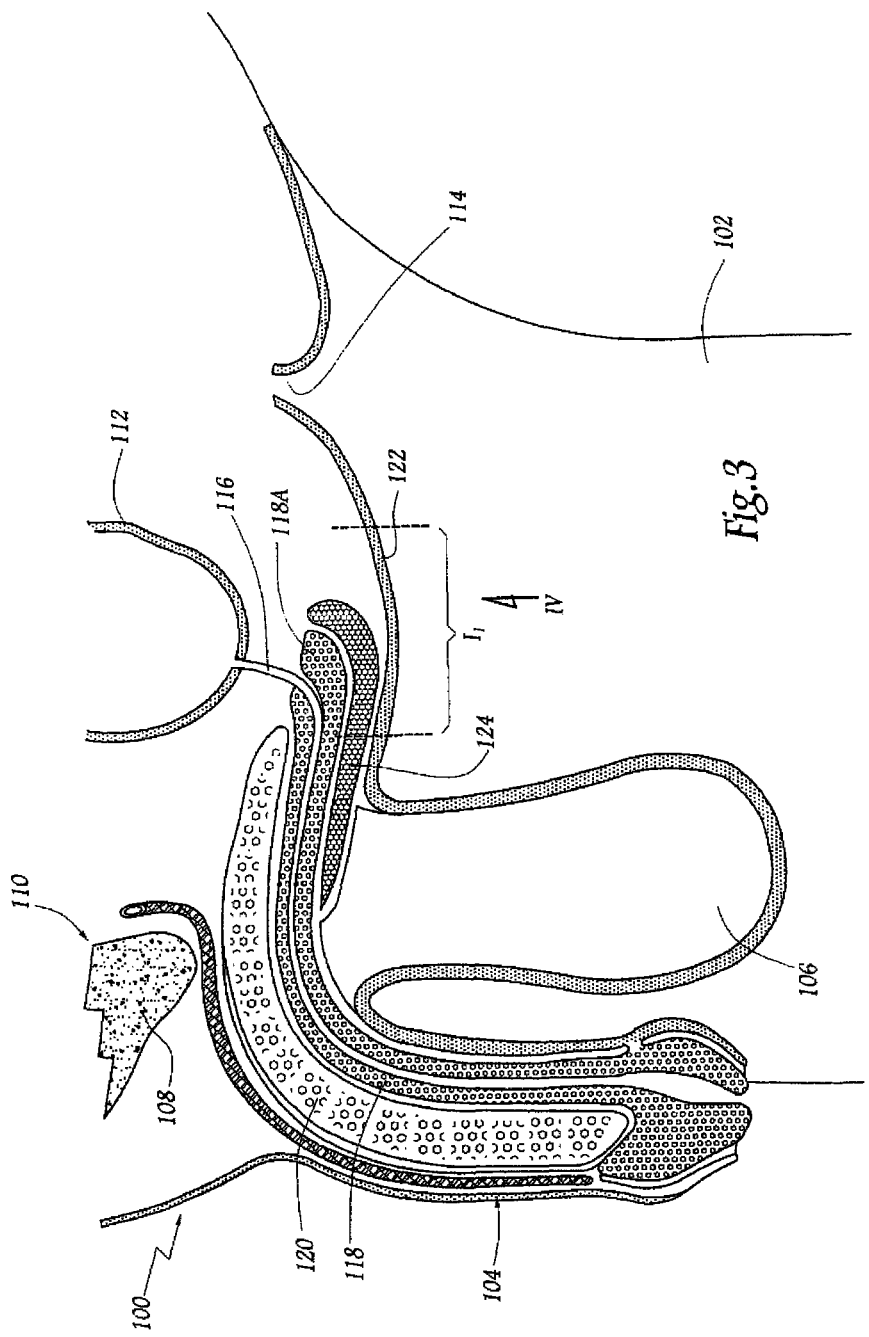
FIG. 3 is a diagrammatic sagittal section of the lower abdomen of a man.

FIG. 1 shows a kit 1 for treating urinary incontinence in a man. The kit 1 comprises a curved needle 10, an elongate strip 20 for supporting the urethra of a patient, and a coil 30 of resorbable suture thread 31.

The needle 10 is made of surgical steel and comprises in succession along its length: a pointed end 11; a curved main portion 12; and a base portion 13 intended more particularly for holding the needle. An optional handle (not shown) may thus be fitted in removable manner on the base portion 13. The needle 10 that is used may present a variety of shapes, in particular concerning its curved portion 12: in the example shown in FIG. 1, the portion 12 lies generally in a single plane, with a profile forming part of a circle in said plane, however other shapes could also be envisaged, such as a shape forming part of a helix.

Along its entire length, the strip 20 is constituted by a knit 21 of biocompatible yarn, with each longitudinal end 21A, 21B thereof being provided with means 22 for securing the needle 10. Various embodiments can be envisaged for the securing means 22: in particular, each means 22 may be in the form of a rigid hollow sleeve adapted to snap around the pointed end 11 of the needle 10, in a circumferential groove 14 formed in the body of the needle at said end. The reader may refer to document EP-A-1 342 450 in the name of the Applicant for details and variant embodiments of such a rigid hollow sleeve, and also for corresponding arrangements in the needle 10.

As shown in greater detail in FIG. 2, the knit 21 is made up of yarn, preferably monofilaments of polypropylene, that are knitted with a predetermined structure comprising essentially: firstly four mutually parallel longitudinal knitted chains 23 forming the reinforcement of the structure; and secondly an open-mesh intermediate trellis 24 that interconnects the chains transversely. This structure enables the knit to be both flexible and non-extensible, so as to enable it to be put into place in the soft tissue of the patient, adapting to the shape of the said tissue, while conferring substantially zero elasticity on the knit in the longitudinal direction, so as to enable the strip to be implanted under high tension.

The structure of the knit 21 also has two opposite lateral fringes 25, each made up of yarns extending outwards from the strip, transversely relative to the corresponding outer chain 23. These fringes 25 are for facilitating connection with anatomical tissue when the strip is implanted in the human body, each of the yarns extending from one or the other of the outer chains 23 advantageously being in the form of a closed loop for limiting irritation of human tissue while the strip is being put into place. The fringes 25 are thus very useful in holding the strip in the tissue of the patient.

The structure of the knit 21 provides large empty spaces between the knitted yarns. In particular, the empty spaces, referenced 26 in FIG. 2, that are defined between each outer chain 23 of the knit and the meshes of the trellis 24 that are furthest from the longitudinal center line 27 of the knit, are each of a size that is capable of having a circle with a diameter of not less than 1 mm geometrically inscribed therein.

FIG. 3 is a simplified diagram of the lower abdomen 100 of a man, together with the outline of the top of one of his thighs 102 in the background. In the sagittal plane corresponding to this figure, there appear in succession, from the front towards the back of the patient, his penis 104, the outline of his scrotum 106, the pubis 108 of his pelvic bone 110, his bladder 112, and his anus 114. The flow of urine from the bladder 112 and out from the penis 104 takes place via the patient's urethra 116. The major portion of the urethra in the longitudinal direction is surrounded by the spongy body 118 of the penis 104, on either side of which there extend lengthwise the two cavernous bodies 120 of the penis. In FIG. 3, only one of the cavernous bodies is shown, it being understood that the two cavernous bodies are situated on either side and in substantially symmetrical manner about the sagittal plane of the patient, while the urethra 116 and the spongy body 118 lie generally centered in said plane.

There follows a description of a surgical method of treating urinary incontinence in the patient whose lower abdomen 100 is shown in FIG. 3, by means of the kit 1 shown in FIGS. 1 and 2.

Immediately before surgery proper, the patient under anesthetic has a urethral probe put into place and is installed in a gynecological position.

Figure 4:
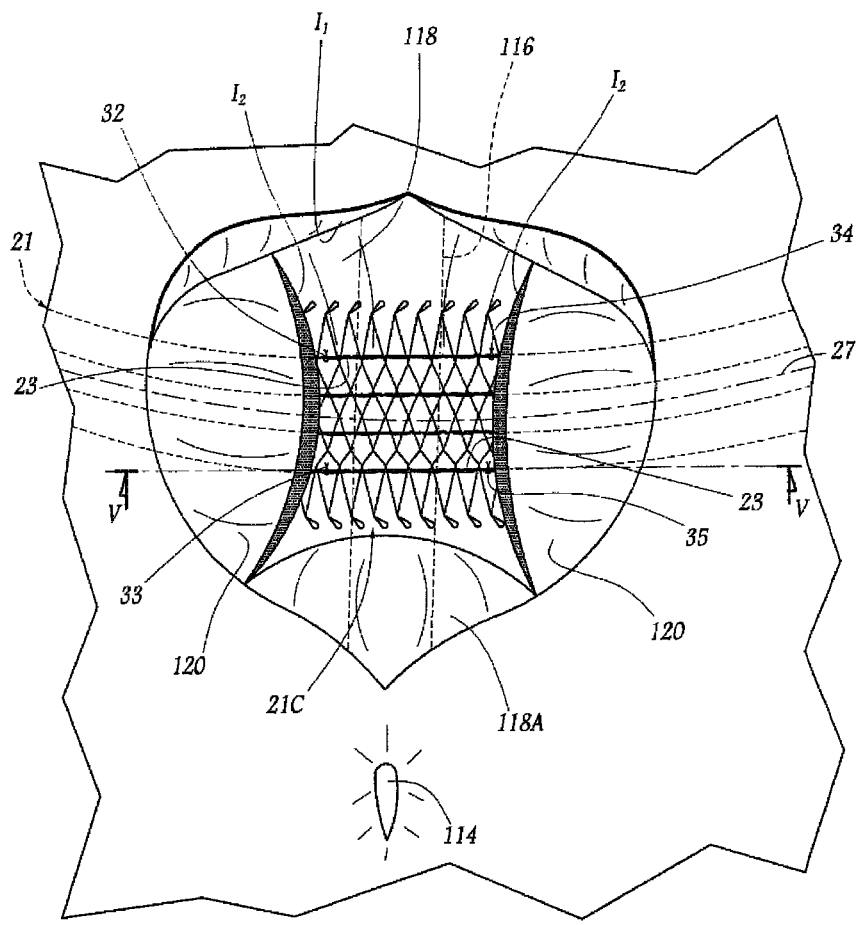
FIG. 4 is an elevation view seen looking along line TV in FIG. 3, showing how the FIG. 1 treatment kit is used.
Figure 5:
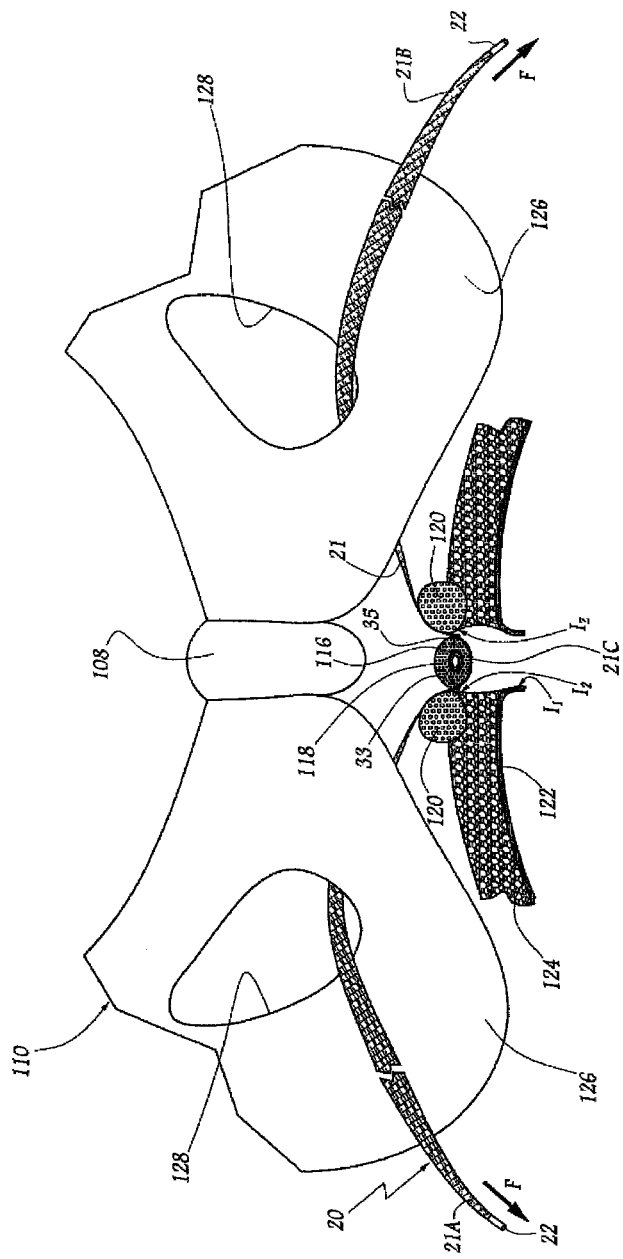
FIG. 5 is a diagrammatic section along line V-V of FIG. 4.

The surgeon vertically incises the perineal region between the anus 114 at the back and the scrotum 106 at the front, as indicated by reference $I_1$ in FIGS. 3 to 5. The front end of the incision $I_1$ is determined by using the finger to find the bottom edge of the pubic bone 108, while the middle of the incision is identified by the bend formed by the urethra 116 going towards the bladder 112, this bend being revealed by the urethral probe. The incision $I_1$ passes upwards both through the skin 112 and the subcutaneous fat 124 in the perineal region, and continues as far as the terminal bulb 118A of the spongy body 118, which is nevertheless preserved. On each lateral side of the bulb, there can then be seen the whitish rounded portions in relief of the fibrous capsules of the cavernous bodies 120. By palpation on either side of the bulb 118A, the surgeon then reveals the V-shaped furrow between each cavernous body 120 and the spongy body 118.

At the bottom of each furrow thus revealed, the perineal membrane is incised in substantially sagittal manner, e.g. using an electric scalpel over a depth of about 1 cm, if possible without penetrating into the corresponding cavernous body 120, as indicated by references $I_2$ in FIGS. 4 and 5. With a finger, the surgeon palpates and gently releases the incised tissue of the membrane, going round the top of each cavernous body 120 so as to come into contact with the corresponding ischio-pubic hip 126 of the pelvic bone.

The surgeon then takes hold of the needle 10 and inserts it into the patient's body starting from the root of a first thigh 102. The entry point for the pointed end 11 of the needle in the root of the thigh is situated both about 4 cm from the incision $I_1$ and at about 4 cm from the projecting bottom edge of the great adductor muscle of the thigh. Because of its curved main portion 12, the needle 10 progresses through the tissue of the patient while remaining on the same lateral side of the patient as the first thigh 102, and until it reaches the corresponding obturator foramen 128 of the pelvic bone, through which the pointed end 11 advances until it reaches the corresponding incision. To do this, the surgeon inserts a finger in the incision $I_2$ so as to feel the approaching pointed end 11 and thus guide its exit through the incision.

Once the pointed end 11 of the needle has gone through the incision $I_2$, the strip 20 is secured to the needle by the securing means 22 snapped into the groove 14, and then the needle is extracted by pulling its base portion 13 so that the end 11 follows the opposite path to that which brought it to the perineal region. The strip 20 is thus put into place in the patient's body between a first one of the two incisions $I_2$ and the root of the first thigh 102 of the patient, passing through a first one of the two obturator foramens 128 of the pelvic bone 110. The needle 10 is thus pulled out until the end 21A of the knit 21 projects outside the patient at the root of his thigh. The surgeon then separates the strip from the needle, by disconnecting the securing means 22.

Using the same needle 10, or an alogous needle, the surgeon performs symmetrical actions on the second lateral side of the patient. The needle is inserted from the root of the second thigh 102 until its pointed end 11 reaches and exits through the second incision $I_2$ in the membrane between the second cavernous body 120 and the spongy body 118, passing via the second obturator foramen 128. The end 21B of the strip is then secured to the pointed end 11 by the corresponding securing means 22. Then by pulling on and withdrawing the needle, the strip is put into place in the patient's body between the second incision $I_2$ and the root of the second thigh 102, passing via the second obturator foramen 128 so that the end 21B of the knit extends out from the patient at the root of his thigh. The strip 120 is then generally in the implantation configuration shown in FIGS. 4 and 5, i.e. it has its center line 27 extending generally perpendicularly to the sagittal midplane of the urethra 116.

The surgeon then puts the strip 20 under tension, i.e., as represented by arrows F in FIG. 5, the surgeon pulls on each of the ends 21A, 21B of the knit 21 so that a middle longitudinal portion 21C of the strip presses firmly against the spongy body 118 from the underside of that body. The portion 21C of the knit 21 then presents a U-shape, with the spongy body 118 being supported in the bottom of the U-shape. The tension exerted on the strip is adjusted so as to obtain obstructive support of the urethra 116, in order to treat incontinence.

Once the surgeon has substantially adjusted the tension in the strip, the strip needs to be anchored in the patient so as to avoid relaxing its effect on the urethra: the surgeon then makes use of the suture thread 31 and secures the portion 21C of the knit 21 to the spongy body 118 at four connection spots given respective references 32 to 35 in FIG. 4. Each connection spot is obtained by introducing a segment of suture thread 31 into one of the empty spaces 26 and making a loop around the corresponding outer chain 23, with a portion of the spongy body 118 being held inside the loop. Passing the suture thread 31 through one of the empty spaces 26 does not damage the structure of the knit 21, since the diameter of the suture thread 31 is smaller than the transverse dimensions of these empty spaces 26. By way of example, the diameter of the suture 31 is 1 mm.

As shown in FIG. 4, the connection spots 32 & 33 and the connection spots 34 & 35 are in alignment on respective directions that are substantially perpendicular to the center line 27 of the knit 21. In this way, any risk of the strip behaving asymmetrically is limited, there being no tendency, for example, for the front of the strip to migrate differently relative to the back of the strip. Furthermore, the connection spots 32 to 35 form a rectangular pattern having an antero-posterior midline that is situated substantially in the mid-sagittal plane of the urethra 116, thus encouraging uniform behavior of the strip on either side of the urethra. Furthermore, by providing for each connection spot 32 to 35 to be closer to one of the sides of the mid-portion 21C than to the center line 27, the major fraction of the width of the knit 21 contributes to the obstructive support force.

Once the strip is tensioned against and secured to the spongy body 118, the surgery comes to an end: the ends 21A and 21B projecting externally at the roots of the thighs 102 are sectioned, with the perineal incision $I_1$ being closed in planes, with prior closure of each incision $I_2$, should that be necessary.

It should be observed that the vertical perineal incision $I_1$ extends substantially perpendicularly to the longitudinal direction of the strip 20 once the strip has been implanted: this approach serves to ensure a good exposition of the implantation zone of the strip and, postoperatively, limits the contact area between the strip and the closure planes of the incision.

In a variant to the above-described surgical method, the step of applying traction to the ends 21A and 21B of the strip 20 and the step of securing the middle portion 21C of the knit 21 by suturing can be performed in the opposite order or in concomitant manner.

Figure 6:
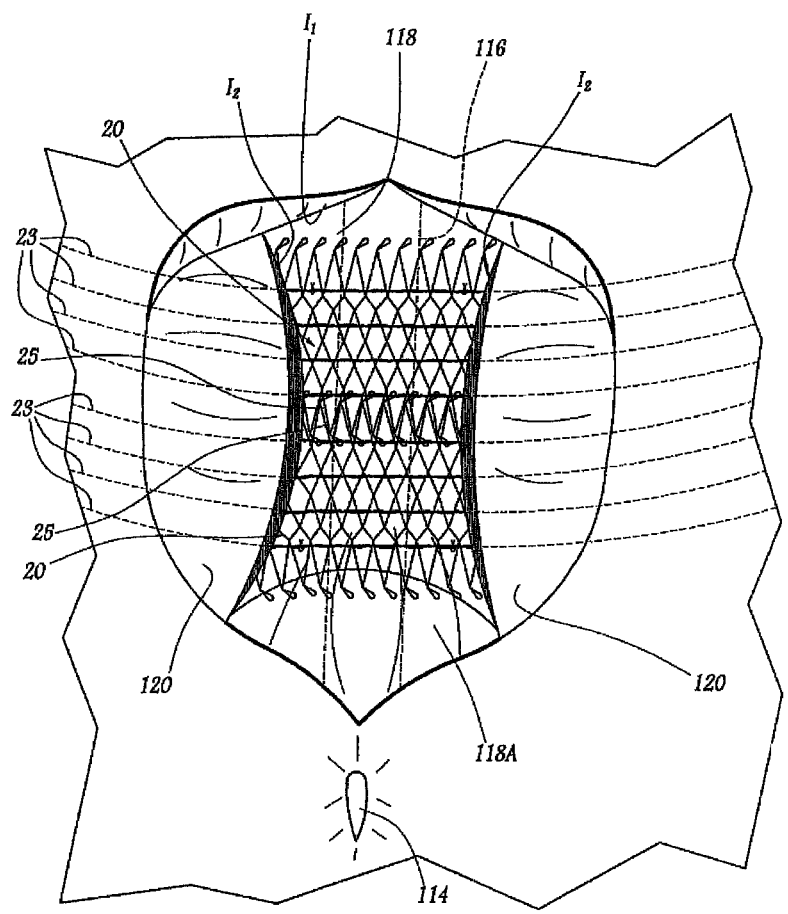
FIG. 6 is an elevation view similar to FIG. 4 showing at least two kit strips connected to one another along their respective outer edges.

A variant that is shown in FIG. 6 consists in simultaneously implanting two strips 20 that are adjacent to each other lengthwise. The main advantage of this disposition is to double the width over which the urethra 116 is supported. In practice, both of the implanted strips need to be capable of being tensioned against and secured to the spongy body 118 without inducing any asymmetrical behavior between the strips relative to each other. For this purpose, the two strips are connected together via their respective adjacent edges. A first practical solution consists, during fabrication of the strips, in tangling together the adjacent fringes 25 of the strips, which amounts to making a "super-strip" in which the knit has eight longitudinal chains 23 that are interconnected both by the intermediate trellises 24 of each of the strips and by the two tangled-together fringes. Another solution consists I suturing together the two outer chains belonging to the two strips. Under such circumstances, and advantageously, the suturing is performed at least in part at one of the connection spots as described above. In this or these spot(s), the two outer chains are secured both to each other and to the spongy body 118, while at least two other connection spots, one anterior and the other posterior are provided respectively for the two strips, it being understood that at least three connection spots are in alignment along a direction substantially perpendicular to th longitudinal direction of the two strips.

Various arrangements and variants to the kit 1 and the treatment method as described above can also be envisaged. By way of example:

- the chains 23 of the strip 20 need not necessarily be four in number, i.e. it is possible to have a greater or smaller number, it being understood that at least two chains are essential for obtaining at least two connection spots, respectively a posterior and an anterior spot;
- insofar as the biological tissue of the patient will tend to colonize the structure of the knit 21, it is sufficient to use a resorbable suture 31; nevertheless, it is possible to envisage using a suture that is not resorbable;
- the knitted structure shown in FIG. 2 need be provided only for the middle portion 21C of the strip 20, since it is only this portion of the strip that is to extend transversely under the urethra and that is to be connected to the tissue under the urethra by segments of suture 31; each free end portion of the strip can thus, in a variant, present a structure that is different, it being understood that the fact of having a strip that is constituted over its entire length by the knit 21 turns out to be practical to make, and also facilitates adjusting the tension of the strip, since the strip then behaves very uniformity along its entire length;
- suturing means other than the suture threads 31 could be envisaged, such as staples, clips, etc., insofar as the suturing means can be connected to the yarn of the knit 21 without damaging it, by passing through the empty spaces 26;
- the number of sutured connection zones 32 to 35 is not necessarily equal to four, although that number turns out to be particularly effective in practice; a solution using only two connection spots is possible, providing the two spots are substantially in alignment in a direction perpendicular to the longitudinal direction of the strip, for reasons of ensuring that behavior is symmetrical in front of and behind the strip, the connection spots then preferably being positioned substantially in the sagittal midplane of the urethra so as to make the behavior of the strip uniform on being subjected to traction on either side of the urethra; and/or
- in addition to suturing the middle portion of the strip 20, it is also possible to suture the ends 21A and 21B, and also intermediate portions thereof between its middle portion and its ends, it being understood that the strip is then secured to other tissue remote from the tissue under the urethra to which connection is made in the spots 32 to 35.

The invention claimed is:

1. A surgical kit for treating urinary incontinence in a man, comprising:

at least one elongate strip for supporting under tension a urethra of a patient, said strip including a longitudinal mid-portion for extending transversely under the urethra when said strip is implanted, wherein said mid-portion is made of a knit of yarns that form an open mesh trellis having empty spaces between the knit yarns, said knit also including reinforcement constituted by at least two spaced longitudinal knitted chains wherein one of the longitudinal knitted chains is closer to an anterior side edge of said mid-portion than a longitudinal centerline of said strip and another of the longitudinal knitted chains is closer to a posterior side edge of said mid-portion than the longitudinal centerline of said strip, said open mesh trellis interconnecting by knitting said at least two longitudinal knitted chains transversely so that said at least two longitudinal knitted chains are attached to said open mesh trellis, said at least two longitudinal knitted chains being more tightly knitted than said open mesh trellis so as to be substantially non-elastically extensible along a longitudinal length thereof whereby the knit is flexible but substantially non-elastic in a longitudinal direction thereof, and suture means adapted to be connected to each of said at least two longitudially knitted chains by introducing a segment of each of said suture means into one of the empty spaces of said trellis and making a loop around the longitudinal knitted chain which loop is adapted to retain a portion of anatomical tissue under the urethra so as to join said at least two longitudinal knitted chains of said mid-portion with the anatomical tissue at at least two connection spots that are respectively located in anterior and posterior lateral parts of said mid-portion and that are in alignment in a direction that is substantially perpendicular to the centerline of said strip when the at least one elongated strip is implanted.

2. A kit according to claim 1, wherein each empty space of said knit, through which said suture means are to pass, has dimensions enabling a circle having a diameter of at least 1 mm to be geometrically inscribed therein.

3. A kit according to claim 1, wherein said knit has a structure such that four connection spots are used to connect said chains, forming a pattern of rectangular or square shape, with a midline that is substantially perpendicular to the centerline of said strip, and such that the midline is designed to be situated in a sagittal midplane of the urethra when said strip is implanted.

4. A kit according to claim 1, wherein said knit has a structure such that only two connection spots are used to connect said chains, such that these two spots are designed to be positioned in a sagittal midplane of the urethra when said strip is implanted.

5. A kit according to claim 1, wherein said strip is constituted over an entire length thereof by said knit.

6. A kit according to claim 1, wherein the yarns of said knit are polypropylene monofilaments.

7. A kit according to claim 1, wherein said suture means includes suture threads individually connected to one of said chains of said knit at one of the connection spots.

8. A kit according to claim 1, wherein said suture means are resorbable.

9. A kit according to claim 1, wherein at least two of said strips are provided which are suitable for being implanted adjacent to each other lengthwise and connected to each other along respective adjacent edges.

10. A surgical method of treating urinary incontinence in a man, by means of a strip for supporting a urethra of a patient, the strip including a longitudinal mid-portion for extending transversely under the urethra when the strip is implanted, wherein the mid-portion is made of a knit of yarns that form an open mesh trellis empty spaces between the knit yarns and wherein the knit also includes reinforcement constituted by at least two longitudinal knitted chains wherein one of the longitudinal knitted chains is closer to an anterior side edge of the mid-portion than a longitudinal centerline of the strip and another of the longitudinal knitted chains is closer to a posterior side edge of the mid-portion than the longitudinal centerline of the strip, and the open mesh trellis transversely interconnects by knitting the chains so that the chains are attached to the open mesh trellis, the at least two longitudinal knitted chains being more tightly knitted than the open mesh trellis so as to be substantially non-elastically extensible along a longitudinal length thereof and such that the knit is flexible but substantially non-elastic in a longitudinal direction thereof, the method comprising the following operative steps:

i) vertically incising skin and subcutaneous fat in a perineal region of the patient, between a scrotum and an anus, up to a bulb of a urethral spongy body, while preserving the spongy body;
  ii) in the perineal incision made during step i), separating the two cavernous bodies of the patient on either lateral side of the urethral spongy body;
  iii) sagittally incising a perineal membrane between each of the two cavernous bodies and the urethral spongy body;
  iv) putting the strip into place in the patient's body so that the mid-portion of the strip extends under and across the urethral spongy body while, on either longitudinal side of said mid-portion, each remaining portion of the strip extends from the corresponding incision in the perineal membrane made in step iii) to a root of the patient's corresponding thigh, passing through a corresponding obturator foramen of the patient's pelvic bone, and two free ends of the strip projecting out from the patient from the respective roots of each of the thighs;
  v) pulling on the two free ends of the strip so as to cause the knit of the mid-portion of the strip to bear without resiliency and under tension against the urethral spongy body;
  vi) connecting suture means to each of the chains of the knit, by introducing a segment of said suture means into one of the empty spaces of the knit and making a loop around the chain, with a portion of the urethral spongy body being held inside the loop, so as to join the chains of the mid-portion of the strip with the urethral spongy body at at least two connection spots which are in alignment in a direction that is substantially perpendicular to the centerline of the strip; and
  vii) sectioning the free ends of the strip that project out at the roots of the thighs and closing the perineal incision made in step i).

11. A method according to claim 10, wherein during step vi), the connection spots to the chains are made so as to form a pattern of rectangular or square shape, with a midline that is substantially perpendicular to the centerline of the strip that is situated in a sagittal midplane of the urethra.

12. A method according to claim 10, wherein step v) is performed before step vi).

13. A method according to claim 10, wherein step v) is performed at least in part after performing all or part of step vi).

* * * * *